(12) United States Patent
Patel

(10) Patent No.: US 9,682,104 B2
(45) Date of Patent: Jun. 20, 2017

(54) LYOPHILIZED PLATELET LYSATES

(75) Inventor: Amit Patel, Salt Lake City, UT (US)

(73) Assignee: Jadi Cell LLC, Salt Lake City, UT (US)

( * ) Notice: Subject to any disclaimer, the term of this patent is extended or adjusted under 35 U.S.C. 154(b) by 0 days.

(21) Appl. No.: 13/358,797

(22) Filed: Jan. 26, 2012

(65) Prior Publication Data

US 2013/0195959 A1  Aug. 1, 2013

(51) Int. Cl.

| | | |
|---|---|---|
| A61L 15/40 | (2006.01) | |
| A61K 35/19 | (2015.01) | |
| A61K 9/19 | (2006.01) | |
| A61Q 19/00 | (2006.01) | |
| A61K 9/00 | (2006.01) | |
| A61K 9/70 | (2006.01) | |
| A61K 8/893 | (2006.01) | |
| A61L 27/36 | (2006.01) | |
| A61L 27/54 | (2006.01) | |

(52) U.S. Cl.
CPC .............. *A61K 35/19* (2013.01); *A61K 8/893* (2013.01); *A61K 9/0078* (2013.01); *A61K 9/19* (2013.01); *A61K 9/7015* (2013.01); *A61L 27/3616* (2013.01); *A61L 27/54* (2013.01); *A61Q 19/00* (2013.01); *A61L 2300/252* (2013.01); *A61L 2300/412* (2013.01)

(58) Field of Classification Search
CPC .......... A61K 35/19; A61K 38/18; A61K 9/19; C12N 5/0644
USPC ........................................................ 424/450
See application file for complete search history.

(56) References Cited

U.S. PATENT DOCUMENTS

| | | | | |
|---|---|---|---|---|
| 5,834,418 | A * | 11/1998 | Brazeau et al. ............. | 514/15.4 |
| 2005/0191286 | A1 | 9/2005 | Gandy | |
| 2006/0051731 | A1 | 3/2006 | Ho et al. | |
| 2006/0142198 | A1* | 6/2006 | Gandy ........................... | 514/12 |
| 2009/0023211 | A1 | 1/2009 | Persson et al. | |
| 2011/0123503 | A1 | 5/2011 | Rebulla et al. | |
| 2011/0171731 | A1 | 7/2011 | Dietz et al. | |
| 2011/0200642 | A1 | 8/2011 | Centeno | |
| 2011/0280952 | A1 | 11/2011 | Caramella et al. | |
| 2012/0276632 | A1 | 11/2012 | Strunk et al. | |

FOREIGN PATENT DOCUMENTS

EP  2540819  1/2013

OTHER PUBLICATIONS

Alemany et al., In vitro evaluation of the hemostatic effectiveness of non viable platelet preparations: Studies with frozen-thawed, sonicated or lyophilized platelets. Vox Sanguinis, vol. 73 (1997) pp. 36-42.*
Gawaz et al. Platelets in inflammation and atherogenesis. Journal of Clinical Investigation, vol. 115 No. 12 (Dec. 1, 2005) pp. 3378-3384.*
Roesken et al., Acceleration of wound healing by topical drug delivery via liposomes. Langenbeck's Archives of Surgery, vol. 385 (2000) pp. 42-49.*
Wolkers et al., Human platelets loaded with trehalose survive freeze-drying. Cryobiology, vol. 42 (2001) pp. 79-87.*
Brinkhous et al., Preservation of platelet receptors for platelet aggregating factor/von Willebrand factor by air drying, freezing, or lyophilization: new stable platelet preparations for von Willebrand factor assays. Thrombosis Research, vol. 13 (1978) pp. 591-597.*
O'Shaughnessey et al., Blood-derived anti-inflammatory protein solution blocks the effect of IL-1β on human macrophages in vitro. Inflammation Research, vol. 60 (2011) pp. 929-936.*
Woodell-May et al., Autologous protein solution inhibits MMP-13 production by IL-1βand TNFα-stimulated human articular chondrocytes. Journal of Orthopedic Research, vol. 29, No. 9 (Sep. 2011) pp. 1320-1326.*
PCT/US2013/023490; filed Jan. 28, 2013; Jadi Cell LLC; international search report dated Jun. 24, 2013.
Crespo-Diaz et al, "Platelet Laysate Consisting of a Natural Repair Proteome Supports Human Mesenchymal Stem Cell Proliferation and Chromosomal Stability", Cell Transplantation, 2011, pp. 797-811, vol. 20, Cognizant Comm Corp.
Mannello et al, "Concise Review: No Breakthroughs for Human Mesenchymal and Embryonic Stem Cell Culture: Conditioned Medium, Feeder Layer, or Feeder-Free; Medium with Fetal Calf Serum, Human Serum, or Enriched Plasma; Serum-Free, Serum Replacement Nonconditioned Medium, or Ad Hoc Formula? All That Glitters is Not Gold!", Stem Cells, 2007, pp. 1603-1609, vol. 25.
Ranzato et al, "Platelet Lysate Modulates MMP-2 and MMP-9 Expression, Matrix Deposition and Cell-To-Matrix Adhesion in Keratinocytes and Fibroblasts", Experimental Dermatology, Oct. 2010, pp. 7, John Wiley & Sons A/S.
Search Report for European application 13740649.2 dated Aug. 7, 2015, 9 pages.

* cited by examiner

*Primary Examiner* — Kara Johnson
(74) *Attorney, Agent, or Firm* — Thorpe North & Western LLP

(57) ABSTRACT

The present disclosure is drawn to compositions and methods of making and using lyophilized platelet lysates. Specifically, a method of preparing a composition suitable for therapeutic use or as a culture medium can comprise steps of concentrating platelets from a platelet source to form a platelet rich portion of the platelet source, and lysing the platelets in the platelet rich portion to form a plurality of lysates. An additional step includes lyophilizing the lysates to form lyophilized platelet lysates in a composition with released concentrations of available growth factors, cytokines, and chemokines. In one example, at 30%, by platelet count, of platelets from a platelet source can be lysed using this process.

19 Claims, 1 Drawing Sheet

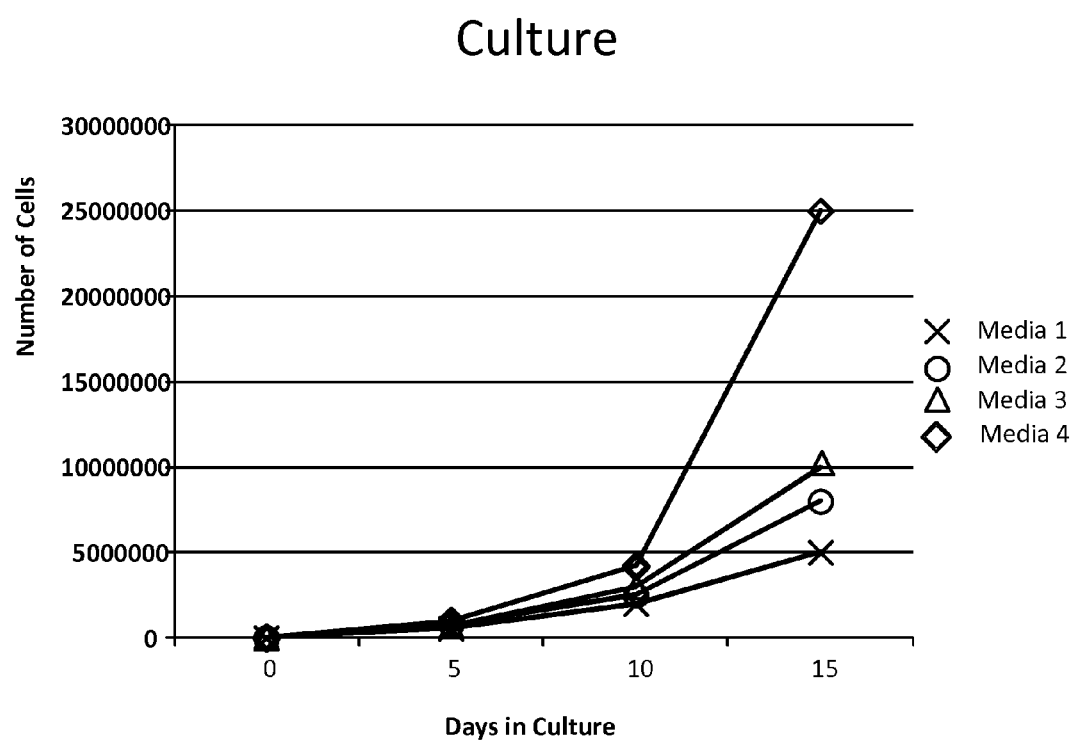

LYOPHILIZED PLATELET LYSATES

BACKGROUND

Several techniques have been described for the preservation and use of platelets. DMSO and trehalose are two examples of compositions that have been used for the preservation of platelets, with or without lyophilization (or freeze-drying). Cryoprotectant compositions have also been used along with lyophilization processes to a similar result. Disadvantages with approaches that merely use preservatives and/or lyophilization on intact platelets relate to the fact that these platelets retain their proteins, receptors, and the like on the surface or within the platelets. For example, several platelet membrane receptors remain intact for binding with extracellular factors in response to platelet activation, e.g., for platelet adhesion, aggregation, etc. Thus, it would be beneficial to prepare a more universal preparation of platelets that can be used effectively for many applications, including wound healing, skin treatment, disorders of body tissue (including body organs) such as lung tissue, or the like.

SUMMARY

A method of preparing a composition suitable for therapeutic use or as a culture medium can comprise steps of concentrating platelets from a platelet source to form a platelet rich portion of the platelet source, and lysing the platelets in the platelet rich portion to form a plurality of lysates. An additional step can include lyophilizing the lysates to form lyophilized platelet lysates in a composition with released concentrations of available growth factors, cytokines, and chemokines. In one example, at least 30%, by platelet count, of platelets from a platelet source can be lysed (during the lysing step and often the lyophilizing step as well) using this process.

In another example, a composition suitable for therapeutic use or as a culture medium can comprise lyophilized platelet lysates prepared from source platelets, wherein the lyophilized platelet lysates provide released concentrations of available growth factor, cytokines, and chemokines. In one example, at least 30% of the source platelets that remain in the composition, by platelet count, are lysed to form the lyophilized platelet lysates.

In another embodiment, a method of treating mammalian tissue can comprise applying a composition including lyophilized platelet lysates to a mammalian tissue site for treatment, wherein the lyophilized platelet lysates include released concentrations of available growth factors, cytokines, and chemokines. In one example, the lyophilized platelet lysates are prepared from source platelets, wherein at least 30% of the source platelets that remain in the composition, by platelet count, are lysed to form the lyophilized platelet lysates.

A method of culturing cells or tissue can comprise admixing a media composition including lyophilized platelet lysates with a cell or tissue culture. The media composition can include lyophilized non-lysed platelets as well, and at least 30% of a total platelet count can make up lyophilized platelet lysates.

BRIEF DESCRIPTION OF THE DRAWING

FIG. 1 sets forth a comparison of mesenchymal stem cell cultures using various types of media, one of which includes lyophilized platelet lysates prepared in accordance with examples of the present disclosure.

DETAILED DESCRIPTION

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the disclosure as illustrated herein, which would occur to one skilled in the relevant art and having possession of this disclosure, are to be considered within the scope of the invention. It is also to be understood that this disclosure is not limited to the particular configurations, process steps and materials disclosed herein, as these may vary to some degree. Further, it is to be understood that the terminology used herein is used for the purpose of describing particular embodiments only, and is not intended to be limiting as the scope of the present disclosure.

It is noted that, as used in this specification and the appended claims, singular forms of "a," "an," and "the" include plural referents unless the content clearly dictates otherwise.

The term "wound" refers to any damage to any tissue of a subject, including damage to the skin as well as damage to deeper tissue, whether the wound is caused accidentally or intentionally, or alternatively by the normal course of a pathological, disease, or degenerative condition. For example, the damage can be as a result of injury or surgery. Non-limiting examples of injuries include ulcers, burns, broken bones, punctures, cuts and scrapes, lacerations, surgical incisions, inflammation, infection, and the like.

As used herein, the term "platelet-containing fluid" refers to any fluid, either biological or artificial, which contains platelets. Non-limiting examples of such fluids include various forms of whole blood, blood plasma, platelet rich plasma, concentrated platelets in any medium, or the like, derived from human and non-human sources.

As used herein, the term "concentrate" or "concentrating" refers to the separation of platelets from the bulk of the plasma, whole blood, or other fluid from which it is present. For example, centrifugation, spectrometry, filtration, decanting, gravity settling, or other methods of concentrating platelets from platelet-containing fluids can be used. When concentrating platelets, it can be desirable to use an anticoagulant (particularly for centrifugation or gravity settling) along with the source of platelets to prevent clotting during the separation of platelets from other components of the blood, plasma, or other fluid.

The term "anticoagulant" refers to compositions that inhibit clotting when concentrating or collecting platelets for use in accordance with examples of the present disclosure. Anticoagulants generally are available as inhibitors of clotting factor synthesis, inhibitors of thrombin, or antiplatelet drugs. Inhibitors of clotting factor synthesis that inhibit the production of certain clotting factors in the liver, include compositions such as warfarin (Coumadin). Inhibitors of thrombin interfere with blood clotting by blocking the activity of thrombin, and include compositions such as heparin and lepirudin (Refludan). Antiplatelet drugs interact with platelets themselves, and include drugs such as aspirin, ticlopidine (Ticlid), clopidogrel (Plavix), tirofiban (Aggrastat), eptifibatide (Integrilin), etc.

The terms "lyophilization," lyophilize," or the like refer to a freeze-drying or dehydration process that is often used to preserve platelets, but is used somewhat differently in accordance with embodiments of the present disclosure. Specifically, lyophilization is used primarily not just as a preservative process, but rather, to further lyse platelets after initial freeze-thaw or other lysis technique is conducted. In other words, in accordance with examples of the present disclosure, after lysates are formed as described herein, lyophilization provides the added benefit of preserving the growth factors, cytokines, chemokines, and other contents initially enclosed within or bound to the surface the platelets, but which are released when platelets are lysed as described herein, e.g., freeze-thaw lysing. The process typically works by freezing the material and reducing surrounding pressure to allow frozen water in the material to sublimate directly from the solid phase to the gas phase.

The term "tissue" includes the full range of small tissue sites to complete organs.

In accordance with the present disclosure, a "lysate" is the composition prepared where platelets are destroyed by disrupting their cell membrane. This can be done chemically, mechanically, by liquid homogenization, or sonication, but in accordance with certain embodiments described herein, the cytolysis is carried out using a freeze-thaw cycle, and to a lesser degree, as part of the lyophilization process. Freeze-thaw lysates can be formed by freezing a platelet suspension and then thawing the material to above room temperature, e.g., 30° C. to 45° C., though other freeze-thaw regimens are also included in the scope of the present disclosure, provided they lead to cytolysis of the platelets. With the freeze-thaw technique, this method causes cells to swell and break as ice crystals form, followed by contraction at thawing. Thus, the cyclical swelling and contracting ultimately causes the platelets to break open. Multiple cycles are typically used for more complete lysis, but the "more complete" lysis is not necessarily required in accordance with examples of the present disclosure. Varying degrees of platelet cytolysis can occur, e.g., at least 30%, at least 50%, at least 70%, at least 90%, or up to 100% cytolosys, by platelet count.

The term "lyophilized platelet lystates" or "LPL" are prepared as described herein. However, it is noted that the term lyophilized platelet lysates also includes "lyophilized platelet rich plasma lysates" or "LPRRL" as a specific type of lyophilized platelet lysates. Thus, any discussion of lyophilized platelet lysates (LPL) also includes lyophilized platelet rich plasma lysates (LPRRL), with the understanding that one difference is that platelet rich plasma is used or formed as part of the method or composition. However, in either composition, both include lyophilized platelet lysates.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of components may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

With these definitions in mind, it has been recognized that the preparation of lyophilized platelet lysates (LPL) and lyophilized platelet rich plasma lysates (LPRPL) can be highly functional for both research and therapeutic applications, either before or after reconstitution in a liquid carrier. When prepared appropriately, these lyophilized platelet lysates can be stable for extended periods of time when frozen, e.g., −80° C., or even at room temperature in certain embodiments. Though these compositions can be useful in both a research and therapeutic environment without the addition of other ingredients, it is noted that both LPL and LPRPL can include one or more active agent or biologic, such as antifungals, antivirals, antibiotics, growth factors, or chemicals depending on the research or therapeutic application. Furthermore, in certain examples, the LPL or LPRPL can be prepared as part of an encapsulated product, e.g., within liposomes. Liposomes, for example, can be prepared that include multilamellar or unilamellar vessicles. In these examples, LPL or LPRPL can be rehydrated at different concentrations ranging 0.01% to 100%, by volume, and mixed with a liposome solution within its hydrophobic membrane.

In accordance with this, a method of preparing a composition suitable for therapeutic use or as a culture medium can comprise steps of concentrating platelets from a platelet source to form a platelet rich portion of the platelet source, and lysing the platelets in the platelet rich portion to form a plurality of lysates. An additional step can further include lyophilizing the lysates to form lyophilized platelet lysates in a composition with released concentrations of available growth factors, cytokines, and chemokines.

In another example, a composition suitable for therapeutic use or as a culture medium can comprise lyophilized platelet lysates prepared from source platelets, wherein the lyophilized platelet lysates provide released concentrations of available growth factor, cytokines, and chemokines. In one example, at least 30% of the source platelets that remain in the composition, by platelet count, are lysed to form the lyophilized platelet lysates. Other concentrations of lyophilized platelet lysates prepared from the source platelets can be at least 50%, 70%, 90%, or even up to 100% lyophilized platelet lysates.

In another embodiment, a method of treating mammalian tissue can comprise applying a composition including lyophilized platelet lysates to a mammalian tissue site for treatment, wherein the lyophilized platelet lysates include released concentrations of available growth factors, cytokines, and chemokines. In one example, the lyophilized platelet lysates are prepared from source platelets, wherein at least 30% of the source platelets that remain in the composition, by platelet count, are lysed to form the lyophilized platelet lysates. Other concentrations of lyophilized platelet lysates prepared from the source platelets can be at least 50%, at least 70%, at least 90%, or even up to 100% lyophilized platelet lysates.

A method of culturing cells or tissue can comprise admixing a media composition including lyophilized platelet lysates with a cell or tissue culture. The media composition can include lyophilized non-lysed platelets as well, and at least 30% of a total platelet count can by lyophilized platelet lysates. Other concentrations of lyophilized platelet lysates prepared from the source platelets can be at least 50%, at least 70%, at least 90%, or even up to 100% lyophilized platelet lysates.

In each of the various embodiments herein, whether discussing the compositions or methods, there may be some common features of each of these examples that further characterize options in accordance with principles discussed herein. Thus, any discussions of the compositions or methods alone are also applicable to the other embodiment not specifically mentioned.

In further detail, the present disclosure provides a method for preparing the lyophilized platelet lysates (LPL), and in one example, LPL can be in the form of lyophilized platelet rich plasma lysates (LPRPL). The platelets can be concentrated using any method known in the art, such as centrifugation or commercially available platelet purification devices. After platelet or platelet rich plasma purification or concentration, a resultant concentrated platelet material can be frozen, such as with liquid nitrogen at −190° C. or to at least −80° C. using dry ice, ethanol, or other freeze assisting composition, for a period of hours, e.g. 24 hours. After freezing, the concentrated platelet material can then be quickly thawed to above room temperature, e.g., from 30° C. to 45° C., or in one example, at about 37° C. This freeze-thaw cycle can be repeated to increase the concentration of platelet lysates. Generally, the more cycles carried out, the more platelets that will be lysed.

Once the platelet lysates are formed using the freeze-thaw cycling procedure or some other lysing process, LPL (or LPRPL) can then be lyophilized using a commercially available lyophilizer, and then stored for extended periods of times at room temperature or even years at below freezing temperatures, e.g., from 0° C. to −100° C., or more specifically in one embodiment, at about −80° C., the product can be stored for about 5 years or more.

In another aspect of the present disclosure, LPL can be used for research applications such as cellular or tissue cultures. Specifically, LPL powder or pellets can reconstituted in a liquid medium (such as DMEM, saline, plasma, DMSO, MEM alpha, RPMI, B-mercaptoethanol, non-essential amino acids, sodium pyruvate, or glutamine, etc.) at appropriate concentrations for a given application. This type of medium, enriched with LPL can be used for culturing mammalian cells, particularly human cells when human platelets are used, for research or therapeutic applications. It should be noted that the use of LPL is useful for growing or deriving various types of cells or tissue, including but not limited to, mesenchymal stem cells from various tissues, human embryonic stem cells, keratinocytes, cardiomyocytes, and many other cell types within the human body, as these lyophilized platelet lysates prepared in accordance with examples of the present disclosure contain growth factors and cytokines that allow growth of cells and tissues, as well as maintain organs and their functions, etc. The growth of cells in LPL supplemented medium, for example, can be an improvement in many cellular systems compared to existing commercially available medium supplements, such as Fetal Bovine Serum (FBS). In addition, LPL cell culture additive can be kept at room temperature for longer periods of time, which is an advantage over FBS, which expires after less than a week at room temperature.

In another aspect of the present disclosure, LPL can be used for many therapeutic applications, such as a supplement in a medium that will be used to culture cells for therapeutic applications. Thus, LPL can be produced as described herein, but under a cGMP system, which results in LPL produced under minimally manipulated methods and/or cGMP. In addition, it is not required that there be any animal products used to produce LPL of the present disclosure, making the material highly useful for human application.

In another aspect of the present disclosure, LPL can be used to treat wounds, ulcers, or burns. As LPL of the present disclosure can be produced under cGMP, topical application to damaged human tissue can be beneficial. As mentioned, LPS can be applied in dry form or rehydrated form prior to application, or as a gel. Alternatively, even if the skin is not damaged by a wound, ulcer, or burn, it can be used for other types of damage that occurs as a result of aging, photodamage, pathological or degenerative disease, or the like. Thus, LPL of the present disclosure can be used at various concentrations and combined with a base cream or other carrier for cosmetic use.

In another aspect, LPL can be rehydrated and nebulized in various concentrations and used to treat lung disorders. Fine powders or rehydrated fine droplets can be inhaled into the lungs for treatment of lung disorders, for example. LPL can also be reconstituted in eye drops as well for treatment of the eyes or surrounding tissue.

In another aspect of the present disclosure, LPL can be rehydrated at any therapeutically effective concentration, or can be kept in powder form, and can be used for orthopedic applications, e.g., bone healing, bone fusion, etc. In yet another aspect, LPL can be combined with a bandage that can be applied to the wound directly, or rehydrated then applied to the wound. Thus, in part due to the relatively long shelf life at room temperature of LPL of the present disclosure, such a bandage has enhanced wound healing properties and will last longer than many other compositions, giving it a better chance to remain active and effective prior to use. Alternatively, other application approaches can also be used, such as by rehydration and application using a syringe, spray bottle, or other solution dispenser at one of any therapeutically effective concentration when applied to the treatment area. Thus, the administration of the therapeutic compositions of the present disclosure can be done in any acceptable manner known in the medical and pharmaceutical arts.

Specific non-limiting examples of administration methods include the use of fluids, aerosols, sprays, mists, lotions, creams, ointments, gels, gums, lozenges, nebulized droplets or powders, suppositories, drops, washes, dispensing bottles, squeeze tubes, pre-soaked fabric, automatic mixing and/or dispensing devices, syringes, bandages, dermal patches or plasters, etc. In one specific example, LPL can be contained in a kit that can be used in combat or other emergency situations for treating wounds. The kit can store LPL in a more stable form, and then can be reconstituted for immediate use when needed.

With specific reference to the lysing cycle that occurs, and where further lysing occurs during the lyophilization step as described herein, increased amounts of growth factors, cytokines, chemokines, etc., can be present in the resultant material. Examples of these growth factors and other materials that can be present in the resultant material include, without limitation, PDGF, PDAF, VEGF, PDEGF, PF-4, TGF-B, FGF-A, FGF-B, TGF-A, IGF-1, IGF-2, BTG, TSP, vWF, PAI-1, IgG, IgM, IgA, KGF, EGF, FGF, TNF, IL-1, KGF-2, fibropeptide A, fibrinogen, albumin, osteonectin, gro-alpha, vitronectin, fibrin D-dimer, favtor V, antithrombin III, a2 macroglobulin, angiogenim, Fg-D, and elastase. In further detail, growth factors, cytokines, or the like that can be present and include, without limitation, LIF, anticancer growth factors such as IGFBP3, eicosanoids such as PGs orleukotrienes, IL-1 TNF alpha, INFs, TNF-a, IL-6, IL-1(a/b), prostanoid metabolites, complement components, reactive oxygen intermediates, arachidonic acid metabolites, coagulation factors, nitrates, and chemokines. Human derived growth factors, chemokines, cytokines, and hormones can include alpha defensin, alpha synuclein, beta synuclean, 4-1 BBL, 6Ckine, acidic FGF, activin A, avtivin R1b, angiopoietin 2, B-DNF, BAFF, BCA-1, BCA-1, BD-1, BMP-2, BMP-4, BMP-7, BMPRA1, BDNF, CNTF, CTGF, CTLA-4Fc, CXCL1, CXCL2, cardiotrophin-1, Cripto, Cystatin C, Dkk-1, EGF AOF, EGF, EMAP II, ENA-78, EPO, Eotaxin, FGF basic AOF, FGF-10, FGF-16, FGF 17, FGF 18, FGF19, FGF4, FGF6, FGF7, FGF8, FGF8b, FGF9, Flt3, G-CSF, GDNF, GMCSF, HGF, HGH, IFN alpha A, IFN alpha A/D, IFN alpha D, IFN alpha a2b, IFN, beta 1A, IFN-gamma, IGF1, IGFII, IGFBP-4, IGFBP6, IL1alpha, IL-1 Beta, IL10, IL11, IL12, IL13, IL15, IL17, IL17A. IL17F, IL18, IL19, IL2, IL20, IL21, IL23, IL28A, IL28B, IL29, IL3, IL31, IL33, IL4, IL5, IL6, IL7, IL8, IL9, IL10, ITAC, KGF2, Kallikrein11, Kallikrein4, Kallikrein7, LEFTY-A, LIF, Leptin, MCSF AOF, MCSF, MCP-1, MCP2, MCP3, MCP4, MDC, MIG, MIP1alpha, MIP1 beta, MIP3 alpha, MIP3 beta, MIP4, MIP5, midkine, NAP2, NT3, NT4, Neurotactin, neurturin, Oncostatin, osteoprotegrerin, PDGF-AA, PDGF-AB, PDGF-BB, PTN, Rank ligand, Rank receptor, RANTES<SCF, SCFAOF, SDF-1 alpha, SDF-1 Beta, CD4, CD40L, TNF-RI, TNFRII, TARC, TECK, TGF alpha, TGF1 Beta1, TGF Beta2, TGF Beta3, TNF beta/lymphotoxin, TNF-alpha, TPO, TRAIL, TWEAK, and VEGF. Thus, the compositions prepared in accordance with examples of the present disclosure can be prepared to remove or destroy the cellular information that is commonly found at the cell membrane, and retain many of these growth factors, cytokines, chemokines, etc., for beneficial use as a healant, cell culture medium additive, cosmetic treatment composition, etc.

EXAMPLES

The following examples illustrate embodiments of the present disclosure that are presently best known. However, it is to be understood that the following are only exemplary or illustrative of the application of the principles of the present disclosure. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what are presently deemed to be the most practical embodiments.

Example 1

Preparation of Lyophilized Platelet Lysates (LPL)

Peripheral blood is collected with an appropriate amount of anticoagulant to prevent clotting of the blood during processing. In this example, 35 mL of blood is collected, which is then centrifuged at 200×g (1000 rpm) for 10 minutes at 4° C. with the brake set to off mode. After centrifugation, the platelet rich portion is removed and tubes of the platelet rich portion are placed into a freezing range of −190° C. to −80° C. for a period of 24 hours. After 24 hours, the platelets are lysed by thawing quickly at 37° C. After thawing, the tubes are then returned for another freeze cycle within the same freezing range for a period of 24 hours. The freeze-thaw cycle (one freeze cycle followed by one thaw cycle) is repeated at least once, and more typically, repeated at least twice for a total 3 cycles, e.g., 3 to 6 freeze-thaw cycles. It is notable that sonication, filtration, or the like, can be used to lyse or collect platelets as well, either alternatively or additively with respect to the freeze thaw cycle described herein. After the last thaw cycle, the tubes are refrozen at −80° C. and stored overnight. The following day, the tubes are lyophilized using FreeZone 2.5 Plus (Labconco) under 0.008 mBar at −84° C. for 48 hrs. The lyophiliziation can further lyse additional platelets as well. Depending on the total volume to be lyophilized, the time may be increased beyond the 48 hours. Likewise, in some embodiments, the time may be decreased to some degree. The LPL, when prepared in this manner, can be stored at room temperature for at least a year, or if at −80° C., for example, a period of 5 years can be possible. It is noted that the steps of lysing and lyophilizing can result in varying degrees of lysed platelets, e.g., 30%, 50%, 70%, 90%, or even up to 100% of the platelets can be lysed, depending varying the number of freeze-thaw cycles, the parameters of the freeze-thaw cycles, the parameters of the lyophilization, etc. Lyophilization alone will not provide the degree of lysing that can occur when conducting both steps of lysing and lyophilizing in accordance with embodiments of the present disclosure.

Example 2

Preparation of Lyophilized Platelet Rich Plasma Lysates (LPRPL)

The procedure of Example 1 is followed, except for with LPRPL, after the blood is collected as previously described, it is processed using a commercially available PRP preparation device such as the Magellan PRP device by Arteriocyte Medical Systems. The lysing and lyophilization steps of Example 1 can be otherwise the same for the present Example.

Example 3

Use of LPL or LPRPL for Culturing Human Mammalian Cells

After preparing the LPL of Example 1 or the LPRPL of Example 2, the material can be used to supplement tissue culture media for human cell culture. For example, a concentration of LPL or LPRPL can range from 0.5% to 20% by volume of total lyophilized LPL or LPRPL used for the cell culture. In one specific example, 10 mL of LPL or LPRPL can be used to prepare 100 mL of media.

In one specific embodiment, cultured human mesenchymal stem cells are isolated from bone marrow and adipose tissue, and a media composition can be prepared as follows:

10 mL lyophilized LPL or LPRPL (about 1 gram)
1 mL of NEAA (100×)
1 mL of Glutamax (100×)
1 mL of Penn/Strep (100×)
97 mL of DMEM LG—without Phenol In this example, the cells are cultured until about 80% confluency and passaged to generate the desired cell number.

Example 4

Use of LPL or LPRPL for Treating Wounds (Rehydrated Method)

After preparing the LPL of Example 1 or the LPRPL of Example 2, the LPL or LPRPL can then be rehydrated in a syringe or a spray bottle at a desired predetermined therapeutic concentration, such as 5%, 10%, 20%, 30%, 40%, 50%, etc., by volume). The concentration can be related to a desired effect, stability, need for specific type of wound to be treated, etc. In any event, the rehydrated LPL or LPRPL is then applied directly onto the site to be treated, and is covered. The application can be a part of one time treatment, or more typically, can be repeated daily, or every three to five days as desired.

Example 5

Use of LPL or LPRPL for Treating Wounds (Non-Rehydrated or Powder Method)

After preparing the LPL of Example 1 or the LPRPL of Example 2, the LPL or LPRPL is ground into a fine powder and applied directly onto a wound or site of treatment without first rehydrating the composition. The wound is covered for treatment at the wound or treatment site. The application can be a part of one time treatment, or more typically, can be repeated daily, or every three to five days as desired.

Example 6

Use of LPL or LPRPL for Treating Wounds Using a Bandage

After preparing the LPL of Example 1 or the LPRPL of Example 2, the LPL or LPRPL is ground into a fine powder and placed into a small porous gauze. The gauze is then attached to an adhesive material to form a bandage. In this condition, the LPL or LPRPL bandage is ready to be applied onto various types of wounds directly. Alternatively, the LPL or LPRPL bandage can be rehydrated with saline or water and then placed onto the wound site.

Example 7

Use of LPL or LPRPL for Treating Lung Disorders

After preparing the LPL of Example 1 or the LPRPL of Example 2, the LPL or LPRPL is ground into a fine powder and then can be rehydrated at various concentrations determined to have a therapeutic effect for a given treatment regimen. In this example, a concentration of 10% by volume was used. For direct treatment to the lungs, the rehydrated LPL or LPRPL is nebulized and inhaled by the patient for a period of 10 minutes.

Example 8

Two-Part Rehydration of LPL or LPRPL

After preparing the LPL of Example 1 or the LPRPL of Example 2, the LPL or LPRPL is ground into a fine powder and placed into one side of a multi-compartment vessel, and on the other side of the vessel, a sterile saline is placed so that the two materials do not contact one another until a seal is broken. Once the seal is broken, the saline mixes with the LPL or LPRPL and they become rehydrated. A spray applicator is then turned to the ON position, and using a pump to press up and down, the reconstituted LPL or LPRPL is applied by spraying directly onto a site to be treated. This is one example of a device that can be used in accordance with examples of the present disclosure. Other devices can also be used for reconstitution and/or application of the LPL or LPRPL described herein.

Example 9

Use of LPL or LPRPL with an Active Agent or Biologic

After preparing the LPL of Example 1 or the LPRPL of Example 2, the LPL or LPRPL is ground into a fine powder or can be rehydrated at various concentrations determined to have a therapeutic effect for a given treatment regimen. The LPL or LPRPL is then admixed with an active agent or biologic, such as an antifungal, antiviral, antibiotic, growth factor, or chemical, depending on the therapeutic or research application. The concentration of active agent or biologic can be any concentration that has a therapeutic effect or meets a research goal that is being considered, without limitation.

Example 10

Comparison of Mesenchymal Stem Cell Cultures Using Various Media

Lyophilized platelet lysates prepared similarly to that described in Example 1 were compared to other media products for culturing mesenchymal stem cells. FIG. 1 graphically shows the results of the study. Specifically, Media 1 included Embryonic Stem Cell (ESC) qualified 10% Fetal Bovine Serum (FBS); Media 2 included 10% Platelet Rich Plasma (PRP); Media 3 included 10% Platelet Lysates (PL); and Media 4 included 5% lyophilized platelet lysates (LPL), each percentage by volume. As can be seen from FIG. 1, the cells cultured in the media including the lyophilized platelet lysates significantly outperformed the cell cultures that did not include lyophilized platelet lysates.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A lyophilized platelet lysate powder composition, comprising:
   at least 30% lysed platelets by platelet count; and
   growth factors, cytokines, and chemokines released from the lysed platelets which are freeze-dried after release from the lysed platelets to form a lyophilized platelet lysate powder composition that is stable for at least one year when stored at room temperature or at least five years when stored at $-80°$ C.,
   wherein the lyophilized platelet lysate powder composition is prepared by at least two freeze-thaw cycles followed by lyophilization.

2. The composition of claim 1, admixed with a liquid medium.

3. The composition of claim 1, formulated for application to a tissue site for therapeutic use.

4. The composition of claim 1, formulated into a medium for a cellular culture.

5. The composition of claim 4, wherein the medium is formulated for in vitro use.

6. The composition of claim 1, formulated into a medium for in vivo use.

7. The composition of claim 1, wherein platelets used to form the lyophilized platelet lysate powder composition is from a mammalian platelet source.

8. The composition of claim 1, wherein platelets used to form the lyophilized platelet lysate powder composition is from a human platelet source.

9. The composition of claim 1, comprising at least 50% lysed platelets by platelet count.

10. The composition of claim 1, comprising at least 70% lysed platelets by platelet count.

11. The composition of claim 1, comprising at least 90% lysed platelets by platelet count.

12. The composition of claim 1, formulated into an encapsulant.

13. The composition of claim 12, wherein the encapsulant is a liposome.

14. The composition of claim 1, admixed with a therapeutic agent, or drug, or a liquid medium.

15. The composition of claim 1, admixed with a culture media or a liquid medium.

16. The composition of claim 1, wherein lyophilized platelet lysate powder composition is prepared by a process of concentrating a source of platelets to form a platelet rich portion; lysing the platelets in the platelet rich portion to form a plurality of lysates; and lyophilizing the lysates to form lyophilized platelet lysate powder composition.

17. The composition of claim 1, wherein the growth factors, cytokines, and chemokines are released by the freeze-thaw cycle and filtration prior to forming the lyophilized platelet lysate powder composition by freeze drying.

18. The composition of claim 1, wherein the growth factors, cytokines, and chemokines are released by the freeze-thaw cycle and sonication prior to forming the lyophilized platelet lysate powder composition by freeze drying.

19. The composition of claim 1, wherein the lyophilized platelet lysate powder composition is stable for at least one year when stored at room temperature.

* * * * *